United States Patent [19]

Krass et al.

[11] Patent Number: 4,528,025
[45] Date of Patent: Jul. 9, 1985

[54] HERBICIDALLY ACTIVE QUINOLINE OR QUINOXALINE ACETOPHENONE OXIME DERIVATIVES

[75] Inventors: Dennis K. Krass, Canal Fulton; Sidney B. Richter, Fairlawn, both of Ohio

[73] Assignee: PPG Industries, Inc., Pittsburgh, Pa.

[21] Appl. No.: 559,598

[22] Filed: Dec. 8, 1983

Related U.S. Application Data

[62] Division of Ser. No. 436,223, Oct. 25, 1982, Pat. No. 4,440,930.

[51] Int. Cl.$^3$ ............... C07D 215/22; C07D 241/44; A01N 43/60; A01N 43/42
[52] U.S. Cl. ...................................................... 71/92
[58] Field of Search ........................... 71/92; 544/354

[56] References Cited

FOREIGN PATENT DOCUMENTS 42750 3/1981 European Pat. Off. .
23785 11/1981 European Pat. Off. .
46467 3/1982 European Pat. Off. .
46468 3/1983 European Pat. Off. .

Primary Examiner—Mark L. Berch
Attorney, Agent, or Firm—Edward J. Whitfield

[57] ABSTRACT

Disclosed are certain herbicidally active quinoline or quinoxaline acetophenone oxime derivatives, herbicidal compositions containing these compounds and the use of such compounds to control the growth of noxious plants, i.e., weeds.

2 Claims, No Drawings

HERBICIDALLY ACTIVE QUINOLINE OR QUINOXALINE ACETOPHENONE OXIME DERIVATIVES

This is a division of application Ser. No. 436,223, filed Oct. 25, 1982, now U.S. Pat. No. 4,440,930.

DESCRIPTION OF THE INVENTION

This invention relates to certain quinoline or quinoxaline acetophenone oxime derivatives of the Formula I:

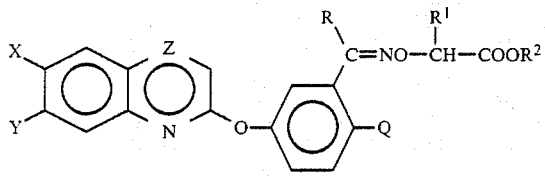

wherein,
R is hydrogen or alkyl of up to 3 carbon atoms which alkyl may be substituted by halogen, cyano, alkoxy or alkylthio;
$R^1$ is hydrogen or methyl;
$R^2$ is hydrogen alkyl of up to 10 carbon atoms or an agronomically suitable ionic species (e.g., sodium, potassium or ammonium);
Q is halogen (e.g., chlorine, bromine or fluorine), nitro, or cyano;
X and Y are the same or different and represent hydrogen, halogen (e.g., chlorine, bromine or fluorine), alkyl or haloalkyl (e.g., trifluoromethyl) of up to 4 carbon atoms; and
Z is nitrogen or —CH—.

Preferred compounds of the Formula I are those wherein at least one of X or Y is halogen, e.g., chlorine, or trifluoromethyl, R is methyl, $R^1$ is hydrogen, and $R^2$ is $C_1$ to $C_4$ alkyl, Z is nitrogen and Q is nitro.

Compounds of this invention embodied in the Formula I are believed to be herbicidally active and would be effective in regulating growth of a wide variety of undesirable plants, i.e., weeds, when applied, in herbicidally effective amount, to the growth medium prior to emergence of the weeds or to the weeds subsequent to emergence from the growth medium. The term "herbicidally effective amount" is that amount of compound or mixture of compounds of this invention required to so injure or damage weeds such that the weeds are incapable of recovering following application. The quantity of compound or mixture of compounds of this invention applied in order to exhibit a satisfactory herbicidal effect may vary over a wide range and depends on a variety of factors, such as, for example, hardiness of a particular weed species, extent of weed infestation, climatic conditions, soil conditions, method of application and the like. Typically, as little as one or less pound per acre of compound or mixture of compounds of this invention would be expected to provide satisfactory weed control, although in some instances application rates in excess of one pound per acre, e.g., up to 5 pounds per acre might be required. Of course, the efficacy of a particular compound against a particular weed species may readily be determined by routine laboratory or field testing in a manner well known to the art.

A compound or compounds of this invention may, of course, be used as such or in formulation with agronomically acceptable adjuvants, inert carriers, other herbicides, or other commonly used agricultural compounds, for example, insecticides, fungicides, stabilizers, safeners, fertilizers or the like. The compounds of this invention alone or in formulation with other agronomically used materials are typically applied in the form of dusts, granules, wettable powders, solutions, suspensions, aerosols, emulsions, dispersions or the like in a manner well known to the art. When formulated with other typically used agronomically acceptable materials, the amount of compound or compounds of this invention may vary over a wide range, for example, from about 0.05 to 95 percent by weight on weight of formulation. Typically, such formulations would contain from about 5 to 75 percent by weight of compound or compounds of this invention.

A compound or compounds of this invention are effective in controlling a variety of common broadleaved and grassy weeds at application rates of only a few grams per acre either pre- or postemergent. Exemplary of weeds that may be effectively controlled by the application of compounds of this invention are barnyard grass (*Echinochloa crusgalli*), crabgrass (*igitaria sauguinalis*), coffeeweed (*Daubentonia punices*), jimsonweed (*Datura stamonium*), johnsongrass (*Sorghum halepense*), tall morningglory (*Ipomoea purpurea*), wild mustard (*Brassica caber*), teaweed (*Sida spinosa*), velvetleaf (*Abutilin Theophrasti*), wild oat (*Avena fatua*), yellow foxtail (*Setaria glauca*), yellow nutsedge (*Cyperus esculentus*) and the like.

The Formula I compounds of this invention may be prepared by reacting an appropriately substituted quinoline or quinoxaline of the Formula II:

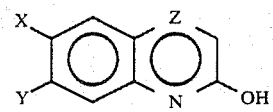

wherein X, Y and Z are as previously defined with a halogenated, preferably fluorinated, aldehyde or ketone of the Formula III:

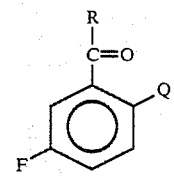

wherein R and Q are as previously defined, to form a compound of the Formula IV:

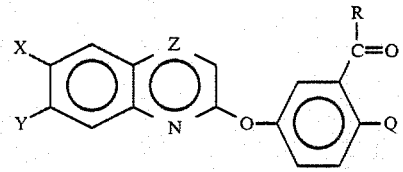

The Formula IV compound is reacted with hydroxylamine or a salt thereof to form the corresponding oxime of the Formula V:

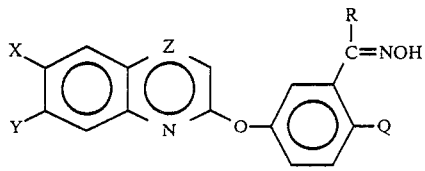

The Formula V compound is then reacted with an α-halocarboxylate of the Formula VI:

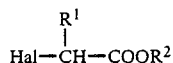

wherein:

Hal is halogen, e.g., bromine or chlorine; and $R^1$ and $R^2$ are as previously defined, to form an invention compound of the Formula I.

The foregoing mode of synthesis is illustrated more specifically as follows:

(a) A reactor is charged with 3.6 grams (0.02 mole) of 6-chloro-2-hydroxy-quinoline (Formula II Compound) in 25 milliliters of dimethylsulfoxide and 2.76 grams (0.02 mole) of anhydrous potassium carbonate. To this mixture is added 3.66 grams (0.02 mole) of 5-fluoro-2-nitroacetophenone (Formula III Compound). After stirring at 60° to 65° C. for about 18 hours, the reaction mixture is stripped of solvent and the residue is dissolved in a mixture of methylene chloride and water. The organic phase is washed with 0.5 normal sodium hydroxide and saturated aqueous sodium chloride solution and dried over anhydrous magnesium sulfate. Filtration and removal of solvent affords 5-(6-chloro-2-quinolinoxy)-2-nitroacetophenone (Formula IV Compound).

(b) A reactor, provided with a Dean-Stark trap and condenser, is charged with 3.42 grams (0.01 mole) of 5-(6-chloro-2-quinolinoxy)-2-nitroacetophenone, prepared as described in part (a), and 25 milliliters each of benzene and ethanol. To this solution is added 1.38 grams (0.02 mole) of hydroxylamine hydrochloride and 2.02 grams (0.02 mole) of triethylamine. After 16 hours at reflux, the reaction mixture is stripped of solvent and the residue is dissolved in a mixture of methylene chloride and water. The organic layer is dried over anhydrous magnesium sulfate affording 5-(6-chloro-2-quinolinoxy)-2-nitroacetophenone oxime (Formula V Compound).

(c) To a reactor containing 25 milliliters of methanol and 0.23 gram of metallic sodium is added 3.57 grams (0.01 mole) of 5-(6-chloro-2-quinolinoxy)-2-nitroacetophenone oxime, prepared as described in part (b). To this stirred mixture is added, dropwise, over a 10 minute period, 1.67 grams (0.011 mole) of methylbromoacetate (Formula VI Compound). After stirring for 18 hours at ambient temperature, the reaction mixture is stripped of solvent and the residue is dissolved in a mixture of methylene chloride and water. The organic phase is dried over anhydrous magnesium sulfate, stripped of solvent and the residue chromatographed on silica gel, affording the desired 5-(6-chloro-2-quinolinoxy)-2-nitroacetophenone oxime-O-(acetic acid, methyl ester).

The manner of preparing a specific compound within the scope of this invention is described in some detail by the foregoing, and it is to be understood that other Formula I compounds can be prepared in like manner by simply varying the choice of starting materials. The compounds of this invention may also be prepared by alternative methods. For example, the compound 5-(6-chloro-2-quinolinoxy)-2-nitroacetophenone oxime-O-(acetic acid methyl ester), prepared as described hereinabove, may also be prepared as follows:

Substantially equimolar amounts of 2,6-dichloroquinoline and the potassium salt of 3-hydroxyacetophenone are reacted, in an inert organic solvent, e.g., dimethylsulfoxide giving 5-(6-chloro-2-quinolinoxy)-acetophenone which is nitrated, with, for example, potassium nitrate in the presence of concentrated sulfuric acid to give the corresponding 2-nitroacetophenone. The 2-nitroacetophenone is then reacted with a suitably substituted aldoxime or ketoxime-O-alkanoic acid, e.g., isopropylidene aminooxyacetic acid in an organic liquid, e.g., acetic acid, reaction medium, and in the presence of a strong organic or mineral acid, e.g., p-toluene sulfonic acid, sulfuric acid or hydrochloric acid, to give 5-(6-chloro-2-quinolinoxy)-2-nitroacetophenone oxime-O-acetic acid. Esterification with an aliphatic alcohol, e.g., methanol, in the presence of a strong organic or mineral acid affords the corresponding 5-(6-chloro-2-quinolinoxy)-2-nitroacetophenone oxime-O-(acetic acid, methyl ester).

Although the invention has been described in some detail with reference to certain embodiments thereof, it is to be understood that it is not intended to be so limited, since many variations may be made therein by those skilled in the art without departing from the spirit and scope thereof as defined in the appended claims.

We claim:

1. In a method of controlling weed growth wherein a herbicidally effective amount of herbicide is applied either to the growth medium prior to emergence of the weeds therefrom or to the weeds subsequent to their emergence from the growth the medium. wherein the improvement resides in using as the herbicide a compound or mixture of compounds of the formula:

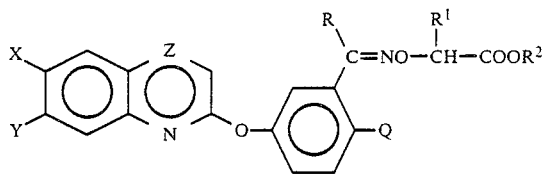

wherein:

R is hydrogen or alkyl of up to 3 carbon atoms which alkyl may be substituted by halogen, cyano, alkoxy or alkylthio;

$R^1$ is hydrogen or methyl, $R^2$ is hydrogen, alkyl of up to 10 carbon atoms or an agronomically suitable ionic species;

Q halogen, nitro, or cyano,

X and Y are the same or different and represent hydrogen, halogen, alkyl or haloalkyl of up to 4 carbon atoms, and Z is nitrogen.

2. A herbicidal composition containing an inert carrier and a herbicidally effective amount of a compound or mixture of compounds of the formula:

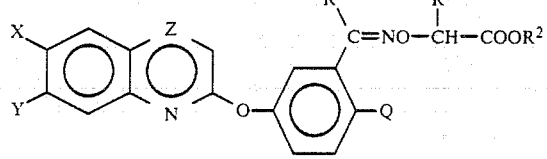

wherein:

R is hydrogen or alkyl of up to 3 carbon atoms which alkyl may be substituted by halogen, cyano, alkxoy or alkylthio;
$R^1$ is hydrogen or methyl,
$R^2$ is hydrogen, alkyl of up to 10 carbon atoms or an agronomically suitable ionic species;
Q halogen, nitro, or cyano,
X and Y are the same or different and represent hydrogen, halogen, alkyl or haloalkyl of up to 4 carbon atoms, and
Z is nitrogen.

* * * * *